United States Patent [19]
Yano et al.

[11] 4,393,134
[45] Jul. 12, 1983

[54] STANDARD BLOOD FILTER PAPER FOR USE IN DIAGNOSIS OF HISTIDINEMIA

[75] Inventors: Akira Yano, Tokorozawa; Yoshitada Saito, Oomiya; Yasushi Kasahara, Tama, all of Japan

[73] Assignee: Fujizoki Pharmaceutical Co., Ltd., Tokyo, Japan

[21] Appl. No.: 424,096

[22] Filed: Sep. 27, 1982

[30] Foreign Application Priority Data

Oct. 7, 1981 [JP] Japan ............................... 56-158629

[51] Int. Cl.³ ........................ C12Q 1/00; G01N 33/68
[52] U.S. Cl. ....................................... 435/29; 422/56; 435/188; 435/805; 435/839; 436/90

[58] Field of Search ...................... 435/18, 23, 29, 32, 435/33, 188, 260, 805, 839; 422/56; 436/89, 90, 176

[56] References Cited

U.S. PATENT DOCUMENTS 3,245,882  4/1966  Guthrie ............................ 422/56 X
4,367,286  1/1983  Saito et al. ...................... 422/56 X Primary Examiner—Arnold Turk
Attorney, Agent, or Firm—Burges, Ryan and Wayne

[57] ABSTRACT

A standard blood filter paper for use in diagnosis of histidinemia, comprising a piece of filter paper, and a blood material infiltrated in the above filter paper containing a known concentration of histidine and at least one salt selected from the group consisting of a dithionite, a disulfite and a bisulfite. The standard blood filter paper can be preserved for a long term at −20° C.

7 Claims, No Drawings

STANDARD BLOOD FILTER PAPER FOR USE IN DIAGNOSIS OF HISTIDINEMIA

This invention relates to a standard blood filter paper for use in diagnosis of histidinemia which is one kind of congenital disorder of amino acid metabolism and more particularly, to a standard blood filter paper of the kind mentioned above, for use in the diagnosis of histidinemia by measuring the concentration of histidine in blood, and which can be preserved for a long period of time without any detectable deterioration.

Congenital disorder of amino acid metabolism, such as histidinemia, phenylketonuria and homocystinuria, are serious diseases leading to mental deficiency or to hepatocirrhosis. These days, however, patients with such congenital disorders can be cured and their lives saved if the disorders are identified during early infancy and the patients are promptly and appropriately treated, for instance, by subjecting them to dietary treatment.

In order to identify those disorders, it is necessary that the concentration of a particular amino acid in the blood of a newborn baby be measured within a week after its birth, to determine whether or not that concentration is abnormally high. For this purpose, there is a need for a simple and reliable screening assay to be developed.

The assay which is in most general use for this determination of amino acid concentration at present is Guthrie's Bacterial Inhibition Assay (Guthrie's test). The principle of this assay is as follows:

When Bacillus subtilis is cultured in an agar culture medium, if the agar culture medium contains a predetermined amount of a metabolism inhibitor which works on an amino acid which is essential to the growth of Bacillus subtilis, the growth of Bacillus subtilis will be inhibited by the action of the metabolism inhibitor. However, when a piece of filter paper into which sample blood was been infiltrated is placed on such an agar culture medium containing the metabolism inhibitor, and Bacillus subtilis is cultured therein, Bacillus subtilis can grow, utilizing the amino acid contained in the blood in the filter paper, so that a growth circle of Bacillus subtilis, corresponding in size to the quantity of the amino acid contained in the blood, is formed.

On the other hand, Bacillus subtilis is cultured on a piece of standard blood filter paper into which blood containing a known amount of the amino acid has been infiltrated, so that a standard growth circle of Bacillus subtilis is obtained.

By comparing the first mentioned growth circle with the second mentioned standard growth circle, the approximate concentration of the amino acid in the sample blood can be determined.

Details of this procedure and of the measurement conditions for the Guthrie's test are described in Rinshobyori (Clinical Pathology) 24 (12), 962-973 (1976).

In order to obtain highly stable and reproducible measurements, it is essential that the amount of the amino acid contained in the standard blood filter paper should not change with time, and that the standard blood filter paper should be preservable for a long period of time without any detectable deterioration. In a conventional standard blood filter paper for measuring the concentration of histidine in the blood, histidine contained in the standard blood filter paper is easily decomposed during preservation. For instance, when it is preserved at a temperature of $-20°$ C., it has so deteriorated after 3 months that it cannot be used any longer. This is a significant shortcoming of the conventional standard blood filter paper.

It is therefore an object of the present invention to provide a novel standard blood filter paper for measuring the concentration of histidine in blood, which standard blood filter paper is free from the shortcomings of the conventional blood filter paper and can be preserved for a long period of time without any detectable deterioration.

The present invention is based on the discovery that particular salts, i.e. dithionites, disulfites and bisulfites are capable of preventing histidine contained in the dried blood from being decomposed, without having any adverse effects on the growth of Bacillus subtilis which serves as an indicator of the quantity of histidine contained in the blood.

Dithionites include sodium hydrosulfite and potassium dithionite. Disulfites are also called metabisulfites or pyrosulfites, and include sodium pyrosulfite and potassium pyrosulfite. Bisulfites are also called hydrogensulfites, and include sodium hydrogensulfite and potassium hydrogensulfite.

A standard blood filter paper embodying the present invention is prepared as follows:

The above salt is dissolved in blood taken from a healthy person so as to yield a mixture of the blood and the salt, containing 10 mM to 50 mM of the salt, preferably 15 mM to 25 mM of the salt, therein.

L-Histidine is dissolved in the thus obtained mixture to yield a mixture with a total concentration of 2 mg/dl of L-histidine. Likewise, seven other analogous mixtures with total concentrations of L-histidine of 4 mg/dl, 6 mg/dl, 8 mg/dl, 10 mg/dl, 12 mg/dl, 16 mg/dl, and 20 mg/dl are prepared.

Each mixture is gently stirred and is then allowed to stand for 2 hours at room temperature so as to disperse the salt and L-histidine homogeneously in the mixture.

Each mixture is spread on a commercially available filter paper for diagnosis of phenylketonuria (PKU) with a diameter of 11 mm and is then air-dried, thereby producing a piece of standard blood filter paper according to the present invention. When the concentration of L-histidine in the blood of a patient is to be measured, a piece of the filter paper with a diameter of 3 mm is cut from the thus produced filter paper by use of a disc puncher, and the disc is employed as a standard in the Guthrie's test.

Unlike the conventional standard blood filter paper, the standard blood filter paper according to the present invention can be preserved without undergoing any detectable deterioration for more than one year at $-20°$ C. or more than 6 months at $4°$ C. And, when preserved under the above-mentioned conditions, can provide a growth circle sized in accordance with the specified amount of L-histidine in the blood therein, without having any adverse effects on the necessary factors for the Guthrie's test, such as the growth of Bacillus subtilis and the color of the blood.

In Table 1, there are shown the results of comparisons between the blood filter papers embodying the present invention and the blood filter papers in which preservatives other than the salts specified for use in the present invention are employed, the results being expressed in terms of the effects of the preservatives on the blood in each filter paper when each filter paper is prepared and on the growth of Bacillus subtilis in the Guthrie's test. The stabilization effects of the preservatives on L-histidine are shown in the last column of Table 1. In this case, the contents of the preservatives are lower than the contents where the effects on the blood and on the growth of *Bacillus subtilis* appear.

ous readings in the comparative observations of the growth of *Bacillus subtilis* in the Guthrie's test.

Moreover, when the preservatives stabilize L-histidine in the blood filter paper, if the preservatives inhibit

TABLE 1

| Preservative | Effects on the Blood | Effects on Guthrie's Test | Stabilization of L-His |
|---|---|---|---|
| β-thiodiglycol | Up to 120 mM, no coagulation of the blood and no change in color of the blood. | Up to 120 mM, no formation of an inhibition circle and no difference in growth of *B. sub.* between the addition of this preservative and no addition thereof. | None |
| β-thiodipropanol | Up to 120 mM, no coagulation of the blood and no change in color of the blood. | Up to 120 mM, no formation of an inhibition circle and no difference in growth of *B. sub.* between the addition of this preservative and no addition thereof. | " |
| Thioglycolic Acid | Above 15 mM, immediate coagulation of the blood, the color thereof changing to dark brown. | Excessive growth of *Bacillus subtilis* not corresponding to the growth of amino acid. | — |
| β, β'-thiodipropionic acid | Above 10 mM, immediate coagulation of the blood, the color thereof changing to dark brown. | Excessive growth of *Bacillus subtilis* not corresponding to the growth of amino acid. | — |
| Dithiothreitol | Above 45 mM, coagulation of the blood in 2 hrs., the color thereof changing to dark brown. | Excessive growth of *Bacillus subtilis* not corresponding to the growth of amino acid. | None |
| 2-mercaptoethyl alcohol | Above 45 mM, coagulation of the blood in 2 hrs., the color thereof changing to dark brown. | Excessive growth of *Bacillus subtilis* not corresponding to the growth of amino acid. | " |
| Sodium thiosulfate | Up to 40 mM, the color of the blood does not change. | Up to 50 mM, no formation of an inhibition circle and no difference in growth of *B. sub.* between the addition of this salt and no addition thereof. | " |
| Sodium hydrosulfite ($Na_2S_2O_4$) | Up to 30 mM, the color of the blood does not change. | Up to 40 mM, no formation of an inhibition circle and no difference in growth of *B. sub.* between the addition of this salt and no addition thereof. | Stabilized |
| Sodium disulfites ($Na_2S_2O_5$) | Up to 30 mM, the color of the blood does not change. | Up to 40 mM, no formation of an inhibition circle and no difference in growth of *B. sub.* between the addition of this salt and no addition thereof. | " |
| Sodium bisulfite ($NaHSO_3$) | Up to 40 mM, the color of the blood does not change. | Up to 80 mM, no formation of an inhibition circle and no difference in growth of *B. sub.* between the addition of this salt and no addition thereof. | " |
| Butylated hydroxyanisole | Practically insoluble in water and difficult to handle. | Forms the same growth circle regardless of the concentration of histidine. | — |
| Butylated hydroxytoluene | Practically insoluble in water and difficult to handle. | Forms the same growth circle regardless of the concentration of histidine. | — |
| EDTA.2Na | The color of the blood does not change. | Above 0.1 mM, inhibition of the growth of *B. sub.* conspicuous. | None |

Referring to Table 1, the preservatives which cause coagulation of the blood are not suitable for the object of the present invention since, if coagulation takes place, the blood is not absorbed homogeneously in the blood filter paper. Furthermore, those preservatives which change the color of the blood placed on the standard blood filter paper to the extent that the color is quite different from the color of the blood to be tested, or those preservatives which form inhibition circles inhibiting the growth of *Bacillus subtilis*, are not suitable for the present invention since they may cause erroneous readings in the comparative observations of the growth of *Bacillus subtilis* or if they promote the growth of the same in a manner which is not related solely to the concentration of histidine contained in the blood, they can also not be used in practice.

The comparative results shown in Table 1 show that preservatives suitable for use in the present invention are dithionites, disulfites and bisulfites.

Referring to Table 2, there are shown the results of tests conducted to show the stability of L-histidine in standard blood filter papers containing the above-mentioned preservatives used according to the present invention, testing being conducted under severe conditions at 37° C. In Table 2, the quantitative measurement of the remaining L-histidine was conducted by Bioassay employing Lactobacillus.

TABLE 2

| Added Amount of L-Histidine | Preservative Added Name | Added Amount | Duration of Stability Test at 37° C. (days) | | | |
|---|---|---|---|---|---|---|
| | | | 2 | 7 | 14 | 24 |
| 6 mg/dl | None (control) | 0 | 5.35 mg/dl (89%) | 4.60 (77) | 4.06 (68) | 3.64 (61) |
| | Sodium hydrosulfite | 20 mM | 5.88 mg/dl (98) | 5.66 (94) | 5.32 (89) | 4.83 (81) |
| | Sodium disulfite | 20 mM | 5.90 mg/dl (98) | 5.70 (95) | 5.26 (88) | 4.77 (80) |
| | Sodium bisulfite | 25 mM | 5.94 mg/dl (99) | 5.70 (95) | 5.44 (91) | 4.92 (82) |
| 12 mg/dl | None (Control) | 0 | 10.8 mg/dl (90%) | 9.05 (75) | 8.26 (69) | 7.00 (58) |
| | Sodium hydrosulfite | 20 mM | 11.77 mg/dl (98%) | 11.25 (94) | 10.56 (88) | 9.55 (80) |
| | Sodium disulfite | 20 mM | 11.76 mg/dl (98%) | 11.14 (92) | 10.50 (88) | 9.46 (79) |
| | Sodium bisulfite | 25 mM | 11.80 mg/dl (98%) | 11.42 (95) | 10.77 (90) | 9.64 (80) |

Note:
Figures in the table indicate the found concentration of residual histidine.
Figures in parentheses indicate ratio of the residual histidine to the amount of histidine added.

It is empirically known that a standard blood filter paper which can retain therein unchanged more than 80% of L-histidine after severe testing for 14 days can be preserved for more than one year at −20° C. and can then be used without any problems for the Guthrie's test. On the basis of this empirical knowledge, it can be assumed from the results in Table 2 that the standard blood filter paper produced by use of the blood to which 20 mM of dithionite, 20 mM of disulfite or 25 mM of bisulfite is added can be safely preserved for more than one year at −20° C.

Referring to Table 3, there are shown the results of tests carried out to investigate the relationship between the amounts of preservatives and the preservation effects achieved. The tests were conducted under the same conditions as the tests summarized in Table 2.

TABLE 3

(i) Sodium hydrosulfite

| Concentration of Histidine | Duration of Preservation at 37° C. (days) | Concentration of Preservative | | | | |
|---|---|---|---|---|---|---|
| | | 5 mM | 10 | 20 | 30 | 40 |
| 6 mg/dl | 14 | 4.60 mg/dl (77%) | 4.94 (82) | 5.41 (90) | 5.50 (92) | 5.42 (90) |
| | 25 | 4.00 (67%) | 4.45 (74) | 4.90 (81) | 4.88 (81) | 4.96 (83) |
| 12 mg/dl | 14 | 9.57 mg/dl (80%) | 10.06 (84) | 10.60 (88) | 10.60 (88) | 10.80 (90) |
| | 25 | 8.12 (68%) | 9.22 (77) | 9.64 (80) | 9.78 (82) | 9.73 (81) |

(ii) Sodium disulfite

| Concentration of Histidine | Duration of Preservation at 37° C. (days) | Concentration of Preservative | | | | |
|---|---|---|---|---|---|---|
| | | 5 mM | 10 | 20 | 30 | 40 |
| 6 mg/dl | 14 | 4.63 mg/dl (77%) | 4.90 (82) | 5.44 (91) | 5.42 (90) | 5.42 (90) |
| | 25 | 4.02 (67%) | 4.38 (73) | 4.82 (80) | 4.81 (80) | 4.90 (82) |
| 12 mg/dl | 14 | 9.50 mg/dl (79%) | 9.85 (82) | 10.70 (89) | 10.71 (89) | 10.83 (90) |
| | 25 | 7.92 (66%) | 8.66 (72) | 9.73 (81) | 9.64 (80) | 9.74 (81) |

(iii) Sodium bisulfite

| Concentration of Histidine | Duration of Preservation at 37° C. (days) | Concentration of Preservative | | | | |
|---|---|---|---|---|---|---|
| | | 10 mM | 20 | 25 | 30 | 50 |
| 6 mg/dl | 14 | 4.78 mg/dl (80%) | 5.22 (87) | 5.44 (91) | 5.46 (91) | 5.50 (92) |
| | 25 | 4.34 (72%) | 4.75 (79) | 4.88 (81) | 4.93 (82) | 4.93 (82) |
| 12 mg/dl | 14 | 9.51 (79%) | 10.58 (88) | 10.82 (90) | 10.90 (91) | 10.92 (91) |
| | 25 | 8.75 (73%) | 9.49 (79) | 9.83 (82) | 9.75 (81) | 9.74 (81) |

As can be seen from Table 3, when more than 20 mM of one of the preservatives is added, the residual amount of L-histidine in the filter paper is more than 80% of the initial amount and, therefore, by the addition of that amount of one of the preservatives, a sufficient preservation effect can be attained.

The present invention is further illustrated by the following Examples.

EXAMPLE 1

6 Liters of the blood (with Haematocrit Value of 42%) from healthy persons was centrifuged at 2000 rpm for 20 minutes. 402 ml of the supernatant solution, blood plasma, was removed from the centrifuged blood by suction, in order to adjust the Haematocrit Value of the remaining blood solution to 55%.

50 ml of 2.5 M sodium bisulfite saline solution was placed in a 5 l volumetric flask, and the above-mentioned blood solution was added to the sodium bisulfite solution to yield exactly 5 l of a mixture of the blood and sodium bisulfite. The concentration of sodium bisulfite in the blood mixture was 25 mM.

The concentration of L-histidine in the blood mixture was measured by an automatic amino acid detector to be 1.3 mg/dl.

Eight L-histidine solutions with different concentration of L-histidine were prepared and 1 ml of each solution was placed in each of eight 100 ml volumetric flasks. Into each flask was placed the above-mentioned blood solution containing the preservative in such an amount as to yield exactly mixtures of 100 ml with the total concentration of L-histidine being 2 mg/dl, 4 mg/dl, 6 mg/dl, 8 mg/dl, 10 mg/dl, 12 mg/dl, 16 mg/dl, and 20 mg/dl.

Each of the mixtures was gently stirred and was then allowed to stand for 2 hours at room temperature in order to disperse the L-histidine homogeneously throughout the mixture.

50 μl of each of the mixtures was dropped on pieces of the filter paper for PKU diagnosis manufactured by Toyo Filter Paper Co., Ltd., in such a manner that the dropped mixture spread in a circle with a diameter of 11 mm.

Each filter paper was dried at room temperature for about 2 hours and was then dried in a vacuum dryer and finally laminated.

The thus prepared filter papers were preserved for 6 months and one year at −20° C. and were compared with the conventional blood filter papers in terms of the growth circle of *Bacillus subtilis* in the Guthrie's test.

The results are shown in the following table.

TABLE 4

| Concentration of Histidine | Preservative | Immediately after production | Preservation for 6 months | Preservation for one year |
|---|---|---|---|---|
| 6 mg/dl | Conventional product | 0 | 20.5mm | 18.0 | 15.5(+) |
|  | Product of the invention | Sodium bisulfite 25 mM | 20.5mm | 20.2 | 20.0 |
| 12 mg/dl | Conventional product | 0 | 26.0mm | 22.5 | 18.8(+) |
|  | Product of the invention | Sodium bisulfite 25 mM | 26.3mm | 26.0 | 26.0 |

Note:
Figures in the above table indicate the diameter of the growth circle of *Bacillus subtilis*.
(+) indicates the formation of an inhibition circle.

EXAMPLE 2

10 ml of 2 M sodium hydrosulfite saline solution was placed in a one liter volumetric flask and the blood solution with the Haematocrit Value of 55%, prepared in Example 1, was added to the sodium hydrosulfite solution to yield exactly 1 l of the mixture. The concentration of the preservative, sodium hydrosulfite, in the mixture was 20 mM. Exactly in the same manner as in Example 1, a predetermined different amount of L-histidine was added to each blood solution to form blood mixtures with different concentration of L-histidine and each mixture was dropped on each piece of the previously mentioned filter paper for PKU diagnosis.

Each filter paper was dried to prepare a standard blood filter paper.

The thus prepared filter papers were preserved for 6 months and one year at −20° C. and were compared with the conventional blood filter papers in terms of the growth circle of *Bacillus subtilis* in the Guthrie's test.

The results are shown in the following table.

TABLE 5

| Concentration of Histidine | Preservative | Immediately after production | Preservation for 6 months | Preservation for one year |
|---|---|---|---|---|
| 6 mg/dl | Conventional product | 0 | 20.0mm | 17.2 (+) | 14.0(+) |
|  | Product of the invention | Sodium hydrosulfite 20 mM | 20.0 | 19.5 | 19.5 |
| 12 mg/dl | Conventional product | 0 | 26.0 | 21.0 | 18.0(+) |
|  | Product of the invention | Sodium hydrosulfite 20 mM | 26.0 | 26.0 | 25.5 |

Note:
Figures in the above table indicate the diameter of the growth circle of *Bacillus subtilis*.
(+) indicates the formation of an inhibition circle.

EXAMPLE 3

10 ml of 2 M sodium disulfite saline solution was placed in a one liter volumetric flask, and standard blood filter papers were prepared in the same manner as employed in Example 2.

As to the standard blood filter papers thus obtained and the conventional blood filter papers, preservation tests at −20° C. were carried out in the same manner as in Examples 1 and 2.

TABLE 6

| Concentration of Histidine | Preservative | Immediately after production | Preservation for 6 months | Preservation for one year |
|---|---|---|---|---|
| 6 mg/dl | Conventional product | 0 | 20.0mm | 17.0 (+) | 14.0(+) |
|  | Product of the invention | Sodium disulfite 20 mM | 20.3mm | 19.7 | 19.5 |
| 12 mg/dl | Conventional product | 0 | 26.5mm | 21.5 | 18.5(+) |
|  | Product of the invention | Sodium disulfite 20 mM | 26.2mm | 25.8 | 25.5 |

Note:
Figures in the above table indicate the diameter of the growth circle of *Bacillus subtilis*.
(+) indicates the formation of an inhibition circle.

We claim:
1. A standard blood filter paper for measuring the concentration of histidine in the blood, comprising:
   a piece of filter paper, and
   a blood material, infiltrated in said filter paper, containing a known concentration of histidine and at least one salt selected from the group consisting of a dithionite, a disulfite and a bisulfite in an amount effective to preserve said histidine.

2. A standard blood filter paper of claim 1, wherein the cation of said salt is sodium or potassium.

3. A standard blood filter paper of claim 2, wherein the concentration of said salt in said blood material is in the range of 10 mM to 50 mM.

4. The standard blood filter paper of claim 1 wherein the dithionite is selected from the group consisting of sodium hydrosulfite and potassium dithionite.

5. The standard blood filter paper of claim 1 wherein the disulfite is selected from the group consisting of sodium pyrosulfite and potassium pyrosulfite.

6. The standard blood filter paper of claim 1 wherein the bisulfite is selected from the group consisting of sodium hydrogensulfite and potassium hydrogensulfite.

7. The standard blood filter paper of claim 3 wherein the concentration of said salt is between 15 mM and 25 mM.

* * * * *